US011867168B2

(12) United States Patent
Tanaka

(10) Patent No.: US 11,867,168 B2
(45) Date of Patent: Jan. 9, 2024

(54) FLUID CONTROL DEVICE AND SPHYGMOMANOMETER

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1201 days.

(21) Appl. No.: 16/522,762

(22) Filed: Jul. 26, 2019

(65) Prior Publication Data
US 2019/0343405 A1 Nov. 14, 2019

Related U.S. Application Data

(63) Continuation of application No. PCT/JP2018/001698, filed on Jan. 22, 2018.

(30) Foreign Application Priority Data

Jan. 31, 2017 (JP) ................................. 2017-015093

(51) Int. Cl.
*F04B 45/047* (2006.01)
*A61B 5/021* (2006.01)
(Continued)

(52) U.S. Cl.
CPC .......... *F04B 45/047* (2013.01); *A61B 5/0225* (2013.01); *A61B 5/02141* (2013.01); *F04B 49/06* (2013.01); *A61B 5/0235* (2013.01)

(58) Field of Classification Search
CPC ........ F04B 45/047; F04B 49/06; F04B 39/06; F04B 41/02; A61B 5/02141; A61B 5/0225; A61B 5/0235
See application file for complete search history.

(56) References Cited

U.S. PATENT DOCUMENTS 5,338,161 A * 8/1994 Eley ........................ F04C 14/26
417/310
8,708,428 B2 * 4/2014 Suzuki .................... F04B 49/06
303/3
(Continued)

FOREIGN PATENT DOCUMENTS

JP  S59-141934 A  8/1984
JP  2001-355574 A  12/2001
(Continued)

OTHER PUBLICATIONS

International Search Report for International Application No. PCT/JP2018/001698 dated Feb. 27, 2018.
(Continued)

*Primary Examiner* — Jason M Sims
*Assistant Examiner* — Mitchell E Alter
(74) *Attorney, Agent, or Firm* — Pearne & Gordon LLP

(57) ABSTRACT

A fluid control device (101) includes a pump (20), a container (70) that is pressurized or decompressed by the pump (20), a valve (60) that allows communication between the container (70) and an outside of the container (70) when the valve (60) is in an opened state, and a controller (90) that controls the pump (20) and the valve (60). The controller (90) pressurizes or decompresses the container (70) by closing the valve (60) and driving the pump (20) and then cools down the pump (20) by opening the valve (60) and driving the pump (20). Accordingly, an increase in the temperature of the pump can be reduced, and convenience of the fluid control device can be improved.

16 Claims, 12 Drawing Sheets

(51) Int. Cl.
*A61B 5/0225* (2006.01)
*F04B 49/06* (2006.01)
*A61B 5/0235* (2006.01)

(56) References Cited

U.S. PATENT DOCUMENTS

| | | | |
|---|---|---|---|
| 2012/0046561 A1* | 2/2012 | Usuda | A61B 5/02116 600/494 |
| 2013/0178752 A1* | 7/2013 | Kodama | F16K 15/145 600/498 |
| 2014/0163402 A1* | 6/2014 | Lamego | A61B 5/022 600/493 |

FOREIGN PATENT DOCUMENTS

| | | |
|---|---|---|
| JP | 2007-42724 A | 2/2007 |
| JP | 2012-107636 A | 6/2012 |
| JP | 5185475 B2 | 4/2013 |
| JP | 2016-200067 A | 12/2016 |

OTHER PUBLICATIONS

Written Opinion for International Application No. PCT/JP2018/001698 dated Feb. 27, 2018.

* cited by examiner

FLUID CONTROL DEVICE AND SPHYGMOMANOMETER

This is a continuation of International Application No. PCT/JP2018/001698 filed on Jan. 22, 2018 which claims priority from Japanese Patent Application No. 2017-015093 filed on Jan. 31, 2017. The contents of these applications are incorporated herein by reference in their entireties

BACKGROUND OF THE DISCLOSURE

Field of the Disclosure

The present disclosure relates to a fluid control device that includes a piezoelectric pump and a sphygmomanometer that includes the fluid control device.

Description of the Related Art

Various fluid control devices including a pump, a pressure container, a valve, and the like have been designed. For example, Patent Document 1 discloses a fluid control device that includes a pump and a valve.

The fluid control device in Patent Document 1 drives a pump and discharges air through a discharge hole of the pump into the valve. Then, the air flows through a cuff connecting port into the cuff (pressure container). Accordingly, the cuff is filled with the compressed air. After that, when the driving of the pump is stopped, the compressed air in the cuff is exhausted.

Patent Document 1: Japanese Patent No. 5185475
Patent Document 2: Japanese Unexamined Patent Application Publication No. 2007-42724

BRIEF SUMMARY OF THE DISCLOSURE

The fluid control device described in Patent Document 1 is used for, for example, a sphygmomanometer. Every time when the blood pressure is measured using the sphygmomanometer, the pressurization of the pressure container caused by the driving of the pump, and the exhaust of the air from the pressure container caused by the release of the valve following the driving of the pump are repeated.

Loss in the pump, except for the energy used for fluid transport when the pump is driven, becomes heat. Therefore, when the pump is driven, the heat is generated at the pump, and the temperature of the pump increases to exceed the temperature outside the pump. When the pump is stopped while air is exhausted from (or air is supplied to) the pressure container, the pump naturally dissipates heat. Therefore, the increased temperature of the pump gradually decreases after the pump is stopped.

However, if the pump does not have a structure suitable for heat dissipation, the heat dissipation speed is slow. Therefore, if such a pump is used repeatedly for a long time, the temperature of the pump gradually increases. Such an increase in the temperature of the pump leads to, for example, the influence on the human bodies (low temperature burn or the like) and the malfunction of the pump.

With a sufficiently long pause time (interval) of the fluid control device, the maximum temperature can be lowered. However, the convenience of the fluid control device is reduced.

Furthermore, when a heat sink described in, for example, Patent Document 2 or the like, is added to a pump, the heat dissipation efficiency increases. Therefore, this configuration is effective in lowering the maximum temperature or shortening the interval of the pump. However, since the size of the pump is increased, this configuration cannot thus be applied to a compact fluid control device.

An object of the present disclosure is to solve the above-described problem and to provide a fluid control device with a reduced increase in the temperature of a pump and an improved convenience of the fluid control device and a sphygmomanometer including the fluid control device.

(1) A fluid control device according to the present disclosure includes a pump; a container that is pressurized or decompressed by the pump; a valve that is able to allow communication between the container and an outside of the container; and a controller that controls the pump and the valve. The controller includes two control modes, which are a first control mode in which the container is pressurized or decompressed by causing the valve to enter a closed state and driving the pump and a second control mode in which the pump is cooled down by causing the valve to enter the opened state and driving the pump. The controller executes the first control mode and then executes the second control mode.

In the state in which the valve is opened, the pump does not pressurize or decompress the container. Meanwhile, in the state in which the valve is opened, the heat of the fluid having the increased temperature in the pump or the heat of the pump itself is effectively exhausted (hereinafter, simply referred to as "cooling") by the fluid discharged from the pump or the fluid sucked by the pump. As described above, after the pressurization or decompression period ends, by forcibly cooling down the pump, the maximum temperature or average temperature for the case where the fluid control device is repeatedly used can be decreased. Thus, the interval can be shortened accordingly.

(2) In the case where a power required for driving the pump is different between a state in which the container is pressurized or decompressed by driving the pump and a state in which the pump is cooled down by driving the pump during a cooling period following pressurizing or decompressing the container, it is preferable that the controller changes a "driving power" that is represented by a power at a time when the pump is continuously driven or an average power in a period in periodical driving of the pump, between the execution of the first control mode and the execution of the second control mode. Accordingly, a predetermined pressurization speed or decompression speed in the valve-closed state can be ensured and a predetermined cooling efficiency in the valve-opened state can be ensured.

(3) In the case where cooling effects need to be increased when the temperature of the pump is increased by the driving of the pump at a time when the container is pressurized or decompressed and the pump is then cooled down by the driving of the pump, during the execution of the second control mode, the controller sets the driving power of the pump to be higher than that during the execution of the first control mode. Accordingly, the pump can be cooled down to a temperature lower than the temperature of the pump immediately after the pressurization or decompression ends, within a shorter period in a shorter interval period.

(4) In the case where the container is pressurized or decompressed by the driving of the pump, in a state in which the pump is driven at a pressurization speed or decompression speed that leads to a problem of the heat generation of the pump, it can be said that the power supplied to the pump is relatively large. In contrast, in a state in which the pump is cooled down by driving the pump during the interval period, a low pressure may be applied to the fluid. Therefore, in many cases, the power supplied to the pump is relatively small. In such a case, during the execution of the second control mode, the controller sets the driving power of the pump to be lower than that during the execution of the first control mode. Accordingly, the maximum temperature for the case where the fluid control device is repeatedly used can be decreased.

(5) In the state in which the pump is cooled down by driving the pump during the interval period, an optimal driving power is set according to the temperature of the pump, in terms of cooling effects. Normally, it is preferable, in terms of increasing the cooling speed, that the power supplied to the pump is increased to quickly cool down the pump to a predetermined temperature in the case where the temperature of the pump is higher than a predetermined temperature, and the power supplied to the pump is decreased to suppress heat generation caused by the driving of the pump and further cool down the pump in the case where the temperature of the pump is lower than the predetermined temperature. Therefore, it is preferable that, after switching from the first control mode to the second control mode, the controller reduces the driving power supplied to the pump step by step.

(6) For example, the driving power for the pump is changed by the controller changing a driving voltage of the pump. The driving power at this time is a fixed value, which is equal to the "driving power".

(7) For example, the driving power for the pump is changed by the controller changing a duty ratio of the driving of the pump. The "driving power" at this time is the average value of the driving power for one period of duty driving.

(8) For example, the driving power for the pump is changed by the controller intermittently driving the pump. The "driving power" at this time is the average value of the driving power for one period of intermittent driving.

(9) It is preferable that the controller changes the driving power for the pump after switching a state of the valve from the closed state to the opened state, in accordance with a temperature of the pump or in accordance with a difference between the temperature of the pump and an ambient temperature. Accordingly, the pump is driven with a power suitable for cooling, and the pump can thus be cooled down effectively.

(10) It is preferable that the controller stops the pump after a predetermined period has passed since switching of a state of the valve from the closed state to the opened state. Accordingly, the driving time of the pump is not unnecessarily increased, and the reliability of the fluid control device can thus be maintained.

(11) It is preferable that, after switching a state of the valve from the closed state to the opened state, the controller stops the pump in accordance with a temperature of the pump or in accordance with a difference between the temperature of the pump and an ambient temperature. Accordingly, the driving time of the pump is not unnecessarily increased, and the reliability of the fluid control device can thus be maintained.

(12) It is preferable that, after the controller switches a state of the valve from the closed state to the opened state, in a case where the temperature of the pump is higher than a predetermined value or in a case where a temperature of the pump is higher than an ambient temperature by a predetermined value or more, the controller drives the pump. Accordingly, the pump is driven during cooling only in a state in which cooling is required. Therefore, unwanted power consumption can be prevented.

(13) The pump is, for example, a piezoelectric pump that transports fluid by vibrations of a piezoelectric element.

(14) A different pump that is connected in series with the pump may be provided. A time during which the different pump is stopped is provided in a time during which the second control mode is executed. With this configuration, the power consumption required for cooling can be reduced, and the amount of the heat generated by driving is decreased. Therefore, cooling effects can be increased.

(15) A sphygmomanometer according to the present disclosure includes the fluid control device as set forth in any one of (1) to (14) described above; a pressure sensor that detects pressure of the container; and a blood flow sensor that detects a state of a blood flow. The container is a cuff. The controller measures blood pressure based on the detection results of the pressure sensor and the blood flow sensor while pressurizing the cuff by closing the valve and driving the pump and while decompressing the cuff by opening the valve.

With this configuration, even in the case where the sphygmomanometer is repeatedly used, an increase in the temperature of the sphygmomanometer (in particular, the pump) can be reduced.

According to the present disclosure, a fluid control device with a reduced increase in the temperature of a pump and an increased convenience, and a sphygmomanometer including the fluid control device can be obtained.

DETAILED DESCRIPTION OF THE DISCLOSURE

Figure 1:
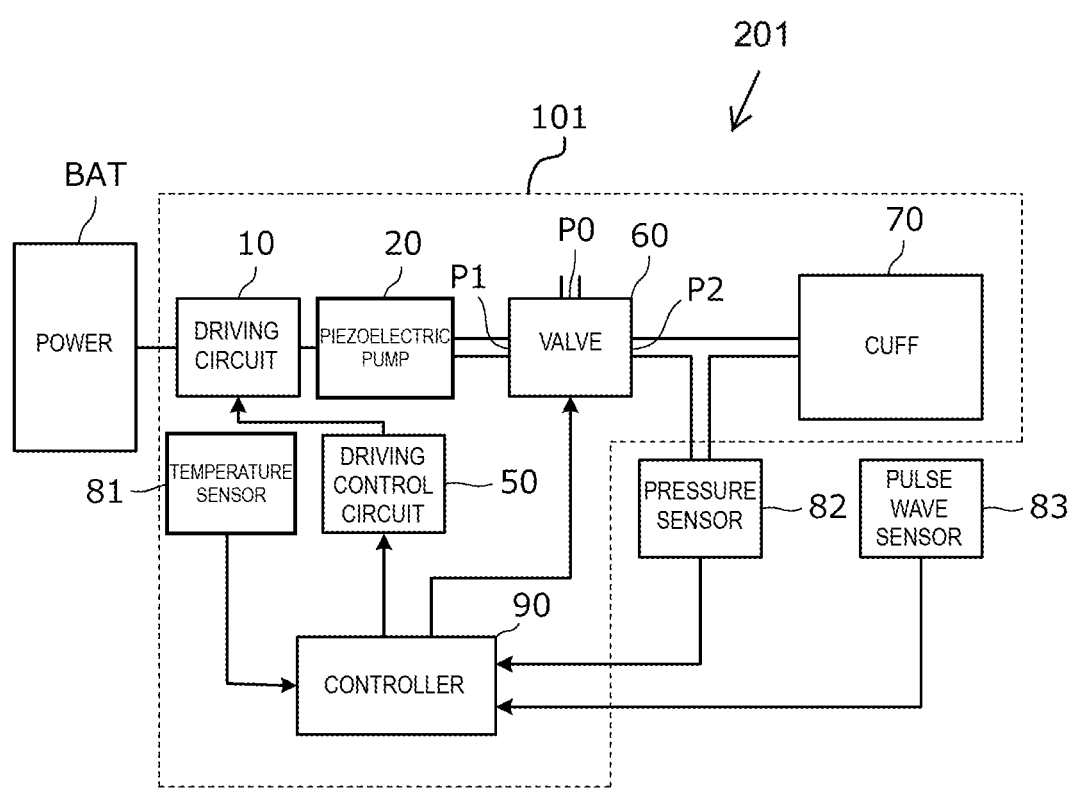
FIG. 1 is a block diagram illustrating a configuration of a fluid control device 101 and a sphygmomanometer 201 according to a first embodiment.

Hereinafter, a plurality of embodiments of the present disclosure will be described by way of specific examples and with reference to drawings. In the drawings, same parts are referred to with the same signs. Taking into consideration describing main points and facilitating understanding, for convenience, separate embodiments will be provided. However, configurations described in different embodiments may be partially replaced or combined. In explanation for embodiments, redundant description of common matters will be omitted, and only differences will be described. Furthermore, similar operations and effects obtained by similar configurations will not be referred to in each of the embodiments.

First Embodiment

FIG. 1 is a block diagram illustrating a fluid control device 101 and a sphygmomanometer 201 according to a first embodiment.

The sphygmomanometer 201 includes a fluid control device 101, a pressure sensor 82, a pulse wave sensor 83, and a power BAT.

The fluid control device 101 includes a piezoelectric pump 20, a cuff 70 that is pressurized by the piezoelectric pump 20, a valve 60 that allows the cuff 70 to communicate with the outside of the cuff 70 when the valve 60 is in an opened state, and a controller 90 that controls the piezoelectric pump 20 and the valve 60. Furthermore, the fluid control device 101 also includes a driving circuit 10 that drives the piezoelectric pump 20, a driving control circuit 50 that controls the driving circuit 10, and a temperature sensor 81 that detects the temperature of the piezoelectric pump 20 or the temperature in the vicinity of the piezoelectric pump 20 and the outside air temperature.

The valve 60 is in a "closed" state when ports P1 and P2 of the valve 60 communicate with each other and port P0 of the valve 60 is closed. However, a state in which there is a slight amount of the flow into and out of the port P0 is also regarded as the closed state. For example, in the case where the amount of the flow generated at the port P0 when a pressure difference of 10 kPa is generated between the port P0 and the port P1 is less than or equal to 10 percent of that in the opened state in the case where a piezoelectric pump is driven at the same voltage and current, is also regarded as the "closed" state. That is, the "closed" state represents a substantially closed state.

Furthermore, a state in which all the ports P0, P1, and P2 communicate with one another represents the "opened" state. In the case where the valve 60 is in the closed state, when the piezoelectric pump 20 is driven, air is sent to the cuff 70. When the valve 60 enters the opened state, air in the cuff 70 is discharged through a path of the valve 60, the port P2→the port P0. Furthermore, when the piezoelectric pump 20 is driven in this state, the air discharged from the piezoelectric pump 20 flows through a path of the valve 60, the port P1→the port P0. As described later, due to the driving of the piezoelectric pump 20 when the valve 60 is in the opened state, the piezoelectric pump 20 is cooled down (exhausts heat).

Figure 2:
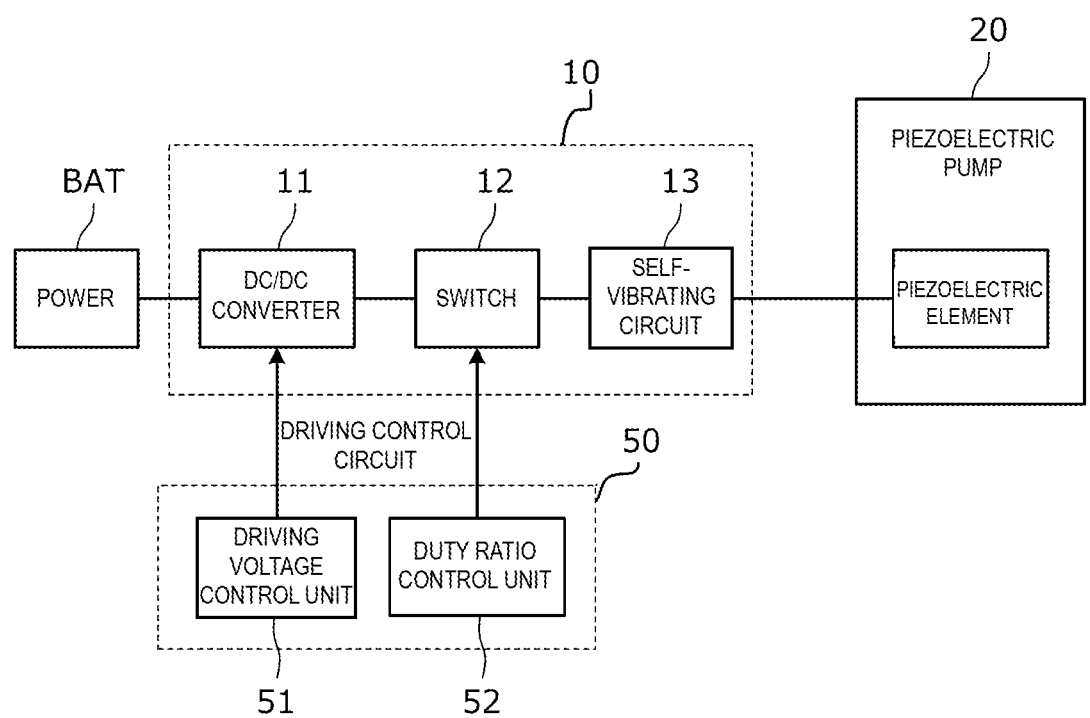
FIG. 2 is a block diagram illustrating a configuration of a piezoelectric pump 20, a driving circuit 10, and a driving control circuit 50 illustrated in FIG. 1.

FIG. 2 is a block diagram illustrating a configuration of the piezoelectric pump 20, the driving circuit 10, and the driving control circuit 50 illustrated in FIG. 1. The piezoelectric pump 20 is a pump that includes a piezoelectric element therein, and transports fluid such as air when the driving voltage is applied to the piezoelectric element and the piezoelectric element thus vibrates. The driving circuit 10 includes a self-vibrating circuit 13 that self-vibrates by being applied with the driving power supply voltage and drives the piezoelectric element of the piezoelectric pump 20, a switch 12 that interrupts the driving power supply voltage (switches between application and non-application of the driving power supply voltage) to the self-vibrating circuit 13, and a DC/DC converter 11 that supplies the driving power supply voltage to the self-vibrating circuit 13. The driving control circuit 50 includes a driving voltage control unit 51 that controls the DC/DC converter 11 to set the output voltage of the DC/DC converter 11 and a duty ratio control unit 52 that controls the switch 12 to set the duty ratio of the driving power supply voltage. The driving voltage of the piezoelectric pump, which will be described later, is set by the driving voltage control unit 51 controlling the ON time and the like of a switching element of the DC/DC converter 11. Furthermore, the duty ratio of the driving of the piezoelectric pump is set by the duty ratio control unit 52 interrupting the switch 12 at a predetermined ON duty ratio.

Figure 3A:
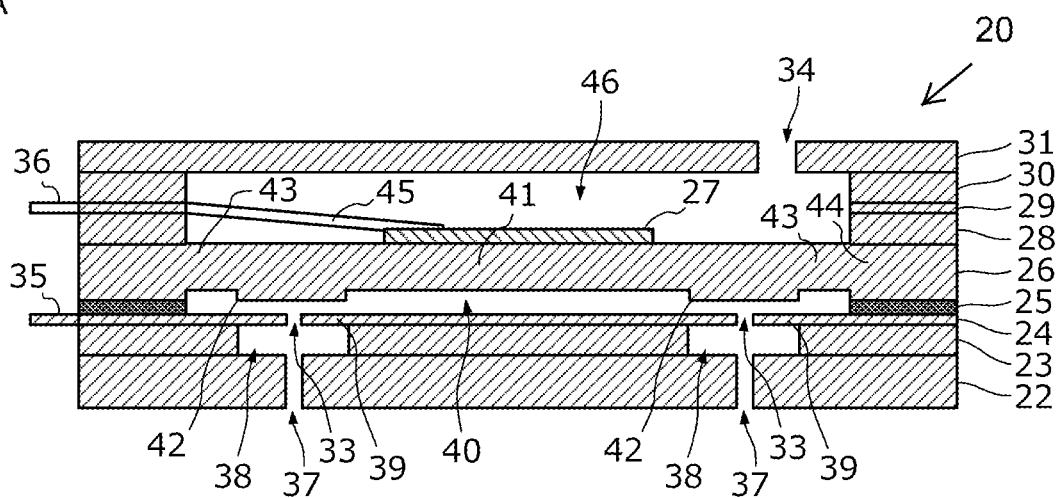
FIG. 3A is a schematic cross-sectional view of the piezoelectric pump 20.

FIG. 3A is a schematic cross-sectional view of the above-mentioned piezoelectric pump 20. The piezoelectric pump 20 includes a cover plate 22, a flow passage plate 23, an opposing plate 24, an adhesive layer 25, a vibration plate 26, a piezoelectric element 27, an insulation plate 28, a power supply plate 29, a spacer plate 30, and a roof plate 31 that are laminated in this order. The piezoelectric pump 20 is thin in the lamination direction and has a rectangular shape in a plan view (when viewed from the lamination direction). A suction port 33 is formed on the cover plate 22 side of the piezoelectric pump 20. A discharge port 34 is formed on the roof plate 31 side of a piezoelectric pump 20. The discharge port 34 of the piezoelectric pump 20 is connected to the port P1 of the valve 60 (see FIG. 1) by a tube or the like.

A flow passage hole 37 of a circular shape is formed at the cover plate 22. A cavity 38 of a circular shape is formed at the flow passage plate 23. The cavity 38 communicates with the flow passage hole 37. The diameter of the cavity 38 is larger than the diameter of the flow passage hole 37. The opposing plate 24 is a metal sheet. An external connection terminal 35 that protrudes outward and the suction port 33, which has a circular shape, are formed at the opposing plate 24. The suction port 33 communicates with the cavity 38. The diameter of the suction port 33 is smaller than the diameter of the cavity 38. Accordingly, a movable part 39 that is bendable is formed around the suction port 33 of the opposing plate 24.

The adhesive layer 25 is formed in a frame shape to overlap a frame part 44 of the vibration plate 26. The adhesive layer 25 has a conductivity and allows the opposing plate 24 and the vibration plate 26 to be electrically connected.

The vibration plate 26 faces the opposing plate 24 with a fixed gap therebetween. The gap between the opposing plate 24 and the vibration plate 26 configures a pump room 40. The vibration plate 26 includes a central part 41, a hitting part 42, a connecting part 43, and the frame part 44. The central part 41 has a circular shape in a plan view and is arranged at the center of the vibration plate 26. The frame part 44 has a frame shape in a plan view and is arranged around the vibration plate 26. The connecting part 43 is a beam shape and allows connection between the central part 41 and the frame part 44. The hitting part 42 has a circular shape in a plan view and is arranged in the vicinity of the border between the central part 41 and the connecting part 43. The hitting part 42 is arranged such that the center of the hitting part 42 faces the suction port 33. The diameter of the hitting part 42 is larger than the diameter of the suction port 33. The hitting part 42 and the frame part 44 are thicker than the central part 41 and the connecting part 43. A cavity (not illustrated in FIG. 3A) surrounded by the components of the vibration plate 26 described above is formed at the vibration plate 26. The pump room 40 communicates with a pump room 46 through the cavity.

The piezoelectric element 27 has a piezoelectricity such that the area of the piezoelectric element 27 expands/contracts in an in-plane direction thereof when an electric filed is applied to the piezoelectric element 27 in the thickness direction thereof. The piezoelectric element 27 has a disk shape and is attached to the upper surface of the central part 41 of the vibration plate 26. An electrode on the lower surface of the piezoelectric element 27 is electrically connected to the external connection terminal 35 with the vibration plate 26, the adhesive layer 25, and the opposing plate 24 interposed therebetween.

The insulation plate 28 is made of an insulating resin. A cavity of a rectangular shape in a plan view is formed at the insulation plate 28. The power supply plate 29 is a metal plate. A cavity of a rectangular shape in a plan view, an internal connection terminal 45 that protrudes into the cavity of the power supply plate 29, and an external connection terminal 36 that protrudes outward are formed at the power supply plate 29. A leading end of the internal connection terminal 45 is soldered onto an electrode on the upper surface of the piezoelectric element 27. The spacer plate 30 is made of resin. A cavity of a rectangular shape in a plan view is formed at the spacer plate 30. The cavities of the insulation plate 28, the power supply plate 29, and the spacer plate 30 communicate with one another to configure the pump room 46.

Figure 3B:
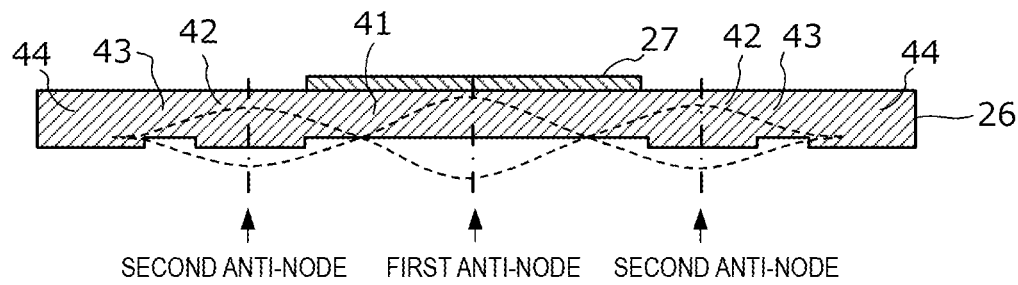
FIG. 3B is a schematic diagram illustrating an operation of the piezoelectric pump 20.

FIG. 3B is a schematic diagram illustrating an operation of the piezoelectric pump 20. In the piezoelectric pump 20, when an AC driving voltage is applied to the external connection terminals 35 and 36, the piezoelectric element 27 moves to expand and contract in an isotropic manner in the in-plane direction, and bending vibrations in a concentric circular shape are generated at a multilayer body of the vibration plate 26 and the piezoelectric element 27 in the thickness direction thereof. The bending vibrations represent a high-order resonant mode in which the frame part 44 serves as a fixed part, the center of the central part 41 serves as a first anti-node, and the center of the hitting part 42 serves as a second anti-node.

Vibrations of the hitting part 42 are transmitted to the movable part 39 by the fluid opposing to the hitting part 42. Vibrations of the hitting part 42 and vibrations of the movable part 39 are coupled so that the fluid flows to the outer peripheral side of the movable part 39 from the vicinity of the suction port 33 in the pump room 40. Accordingly, negative pressure is generated around the suction port 33 in the pump room 40, and the fluid is sucked into the pump room 46 through the suction port 33. Furthermore, positive pressure is generated inside the pump room 46, and the positive pressure is released through the discharge port 34 of the roof plate 31. Therefore, the fluid sucked into the pump rooms 40 and 46 through the suction port 33 flows out of the pump rooms 40 and 46 through the discharge port 34.

Figure 4:
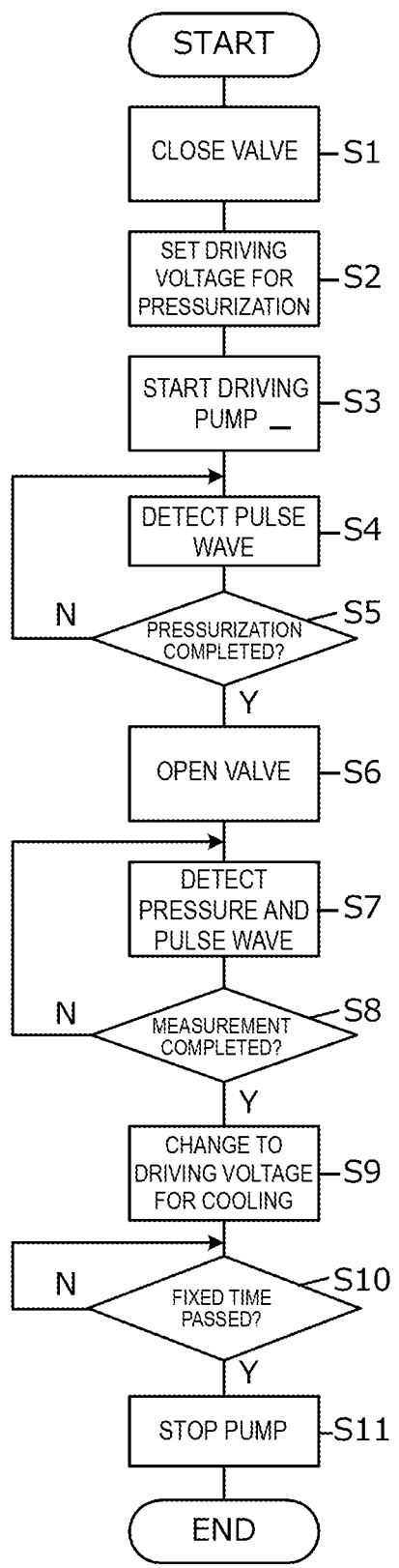
FIG. 4 is a flowchart illustrating a procedure of a process of a controller 90 illustrated in FIG. 1.

FIG. 4 is a flowchart illustrating a procedure of a process of the controller 90 illustrated in FIG. 1. Operations of the fluid control device 101 and the sphygmomanometer 201 will be explained below with reference to FIG. 4.

First, the valve 60 is closed (S1). That is, the ports P1 and P2 of the valve 60 illustrated in FIG. 1 communicate with each other, and the port P0 is closed. Then, a driving voltage for the pressurization is set, and the piezoelectric pump 20 is driven at the set driving voltage (S2→S3). Accordingly, air is sent to the cuff 70, and the pressurization starts.

After that, a detection value of the pulse wave sensor 83 is read. If it is detected, based on the read detection value, that the cuff 70 has reached a predetermined pressure, the valve 60 is opened (S4→S5→S6). That is, all the ports P0, P1, and P2 of the valve 60 illustrated in FIG. 1 communicate with one another. Accordingly, the air inside the cuff 70 is gradually exhausted. During the exhaust, a detection value of the pressure sensor 82 and a detection value of the pulse wave sensor 83 are read, so that the maximum blood pressure and the minimum blood pressure are measured (S7→S8).

After that, the driving voltage of the piezoelectric pump 20 is changed to a driving voltage for cooling (S9). Accordingly, the air discharged from the piezoelectric pump 20 flows through a path of the valve 60, the port P1→the port P0, and the heat of the piezoelectric pump 20 thus starts to be exhausted. That is, the piezoelectric pump 20 starts to cool down by itself.

After that, the process waits for a fixed time, and then, the driving of the piezoelectric pump is stopped (S10→S11).

The driving voltage for cooling may be the same as the driving voltage for pressurization. Alternatively, the driving voltage for cooling may be lower or higher than the driving voltage for pressurization. However, it is desirable that the average driving power supplied to the piezoelectric pump during a cooling period be smaller than the average driving power supplied to the piezoelectric pump during a pressurization period. This configuration is desirable to achieve the cooling effects during the cooling period.

The driving voltage for cooling may be a predetermined value or may be set according to the temperature of the piezoelectric pump or according to a difference between the temperature of the piezoelectric pump and the ambient temperature. For example, as the temperature of the piezoelectric pump increases or the temperature of the piezoelectric pump relative to the ambient temperature increases, a higher driving voltage for cooling may be set.

Furthermore, the cooling period, which is the fixed time, may be a predetermined time or may be set according to the temperature of the piezoelectric pump or according to a difference between the temperature of the piezoelectric pump and the ambient temperature. For example, as the temperature of the piezoelectric pump increases or the temperature of the piezoelectric pump relative to the ambient temperature increases, a longer cooling period may be set.

Figure 5A:
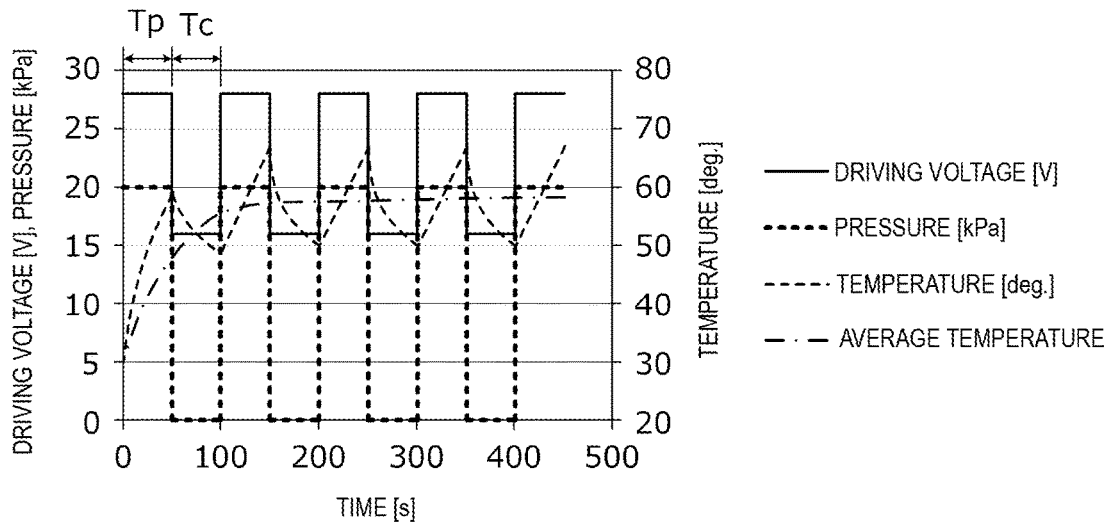
FIG. 5A is a graph illustrating the effects of cooling.
Figure 5B:
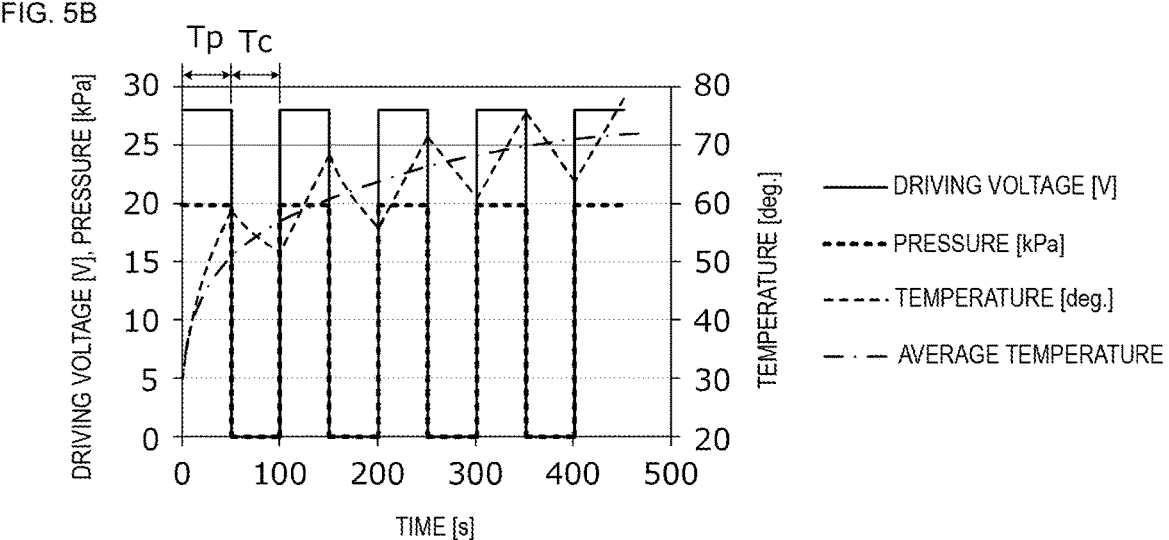
FIG. 5B is a comparative example of that in FIG. 5A.

FIG. 5A is a graph illustrating the effects of the cooling mentioned above, and FIG. 5B illustrates a comparative example of that in FIG. 5A. In FIGS. 5A and 5B, the vertical axis represents the driving voltage of the piezoelectric pump 20, the discharge pressure of the piezoelectric pump 20, and the temperature of the piezoelectric pump 20, and the horizontal axis represents time (elapsed time).

In the first embodiment, the driving voltage during a pressurization period Tp is set to 28 V, and the driving voltage during a cooling period Tc is set to 16 V. A cycle of the pressurization period Tp and the cooling period Tc is repeated. In the comparative example illustrated in FIG. 5B, the driving voltage during the pressurization period Tp is set to 28 V, and the driving voltage during the cooling period Tc is set to 0 V (driving stopped). A cycle of the pressurization period Tp and the cooling period Tc is repeated. The pressurization period Tp and the cooling period Tc are each set to 50 seconds.

In the comparative example, as expressed in the transition of temperature in FIG. 5B, the temperature of the piezoelectric pump 20 increases during the driving of the piezoelectric pump 20, and the temperature of the piezoelectric pump 20 decreases during the stoppage of the piezoelectric pump 20. However, the temperature increase during the driving is larger than the temperature decrease during the stoppage. Therefore, the average temperature of the piezoelectric pump 20 gradually increases and reaches the maximum temperature of about 80 degrees C.

In the first embodiment, as expressed in the transition of temperature in FIG. 5A, the temperature increase during the driving of the piezoelectric pump 20 is substantially the same as that in the comparative example, whereas the temperature decrease during exhaust is larger than the temperature decrease during the stoppage in the comparative example. Therefore, in the process of the repetition of the cycle mentioned above, the average temperature transitions at low levels, and the maximum temperature does not exceed about 70 degrees C.

As is clear from FIGS. 5A and 5B, according to the first embodiment, the maximum temperature and the average temperature of the piezoelectric pump for the case where the fluid control device is repeatedly used can be maintained low. Thus, the interval time for the case where the sphygmomanometer is repeatedly used can be shortened accordingly.

Figure 6A:
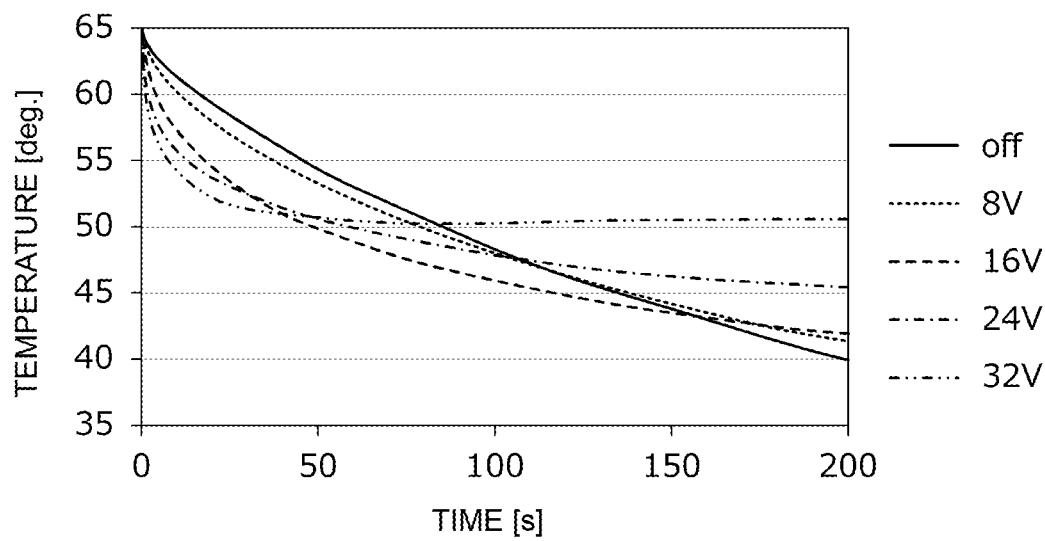
FIGS. 6A and 6B are graphs illustrating the differences in cooling effects of the piezoelectric pump 20 when cooling is performed.
Figure 6B:
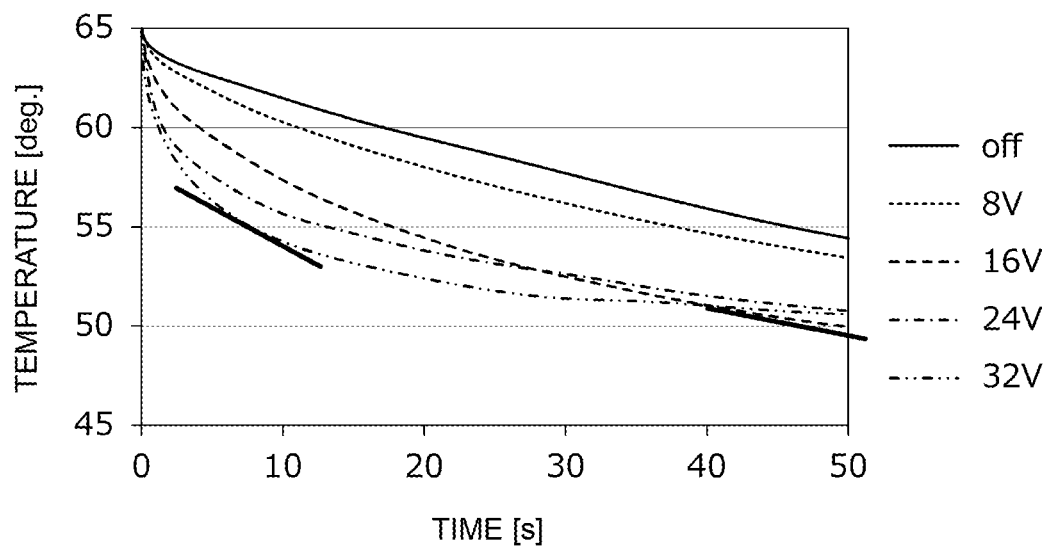

FIGS. 6A and 6B are graphs illustrating the differences in the cooling effects of the piezoelectric pump 20 during cooling. In FIGS. 6A and 6B, the vertical axis represents the temperature of the piezoelectric pump 20, and the horizontal axis represents time (elapsed time). FIG. 6B and FIG. 6A are different only in the scale of the time axis and illustrate the same characteristics. In this example, the relationship of the driving voltage and the discharge amount and power consumption of the piezoelectric pump 20 is set as described below.

During driving at 8 V: 0.24 L/min, 0.11 W
During driving at 16 V: 0.77 L/min, 0.46 W
During driving at 24 V: 1.28 L/min, 1.31 W
During driving at 32 V: 1.87 L/min, 2.75 W The temperature at the start time of cooling is 64 degrees C. During the period from the start of cooling to the time about 40 seconds after the start of cooling, cooling is done at the fastest speed at the time when the driving voltage of the piezoelectric pump 20 for cooling is 32 V. Furthermore, during the period from the time about 40 seconds after the start of cooling to the time about 150 seconds after the start of cooling, the temperature drops to the lowest level at the time when the driving voltage of the piezoelectric pump 20 is 16 V. Furthermore, during a period range of about 150 seconds or more after the start of cooling, the temperature drops to the lowest level at the time when the driving voltage of the piezoelectric pump 20 is 0 V, that is, when the piezoelectric pump 20 is stopped.

A line segment that is in contact with a curve representing the temperature transition represents the inclination of the curve at a corresponding position. Regarding a change in the angle of inclination of the curve from the start of cooling, within a range from 64 degrees C. to 55 degrees C., the maximum angle of inclination is obtained at a driving voltage of 32 V. Furthermore, within a range from 55 degrees C. to 50 degrees C., the maximum angle of inclination is obtained when the driving voltage is within a range from 24 V to 16 V. That is, when the temperature is divided into ranges, driving at 32 V is most effective for cooling within a range from 64 degrees C. to 55 degrees C., and driving within a range from 24 V to 16 V is most effective for cooling within a range from 55 degrees C. to 50 degrees C.

When the piezoelectric pump 20 is driven, cooling down is performed in accordance with the exhaust flow rate, and heat is generated in accordance with the power consumption. Therefore, obtaining a large flow rate by high power driving is effective at a high temperature because a high cooling effect is achieved by exhaust, whereas obtaining a small flow rate by low power driving is effective at a low temperature because a cooling effect by exhaust is low.

As described above, different cooling effects are obtained according to the driving voltage of the piezoelectric pump 20 for cooling. Therefore, a driving voltage at which a high cooling effect can be achieved may be set in accordance with the operating rate (pressurization period/operating period) of the piezoelectric pump 20. The above-mentioned "operating period" is, for example, a period from the start of pressurization for blood pressure measurement to the start of pressurization for the next blood pressure measurement.

Second Embodiment

In a second embodiment, an example in which driving voltage is changed during a cooling period is described. The basic configuration of a fluid control device and a sphygmomanometer according to the second embodiment is the same as that described in the first embodiment.

Figure 7:
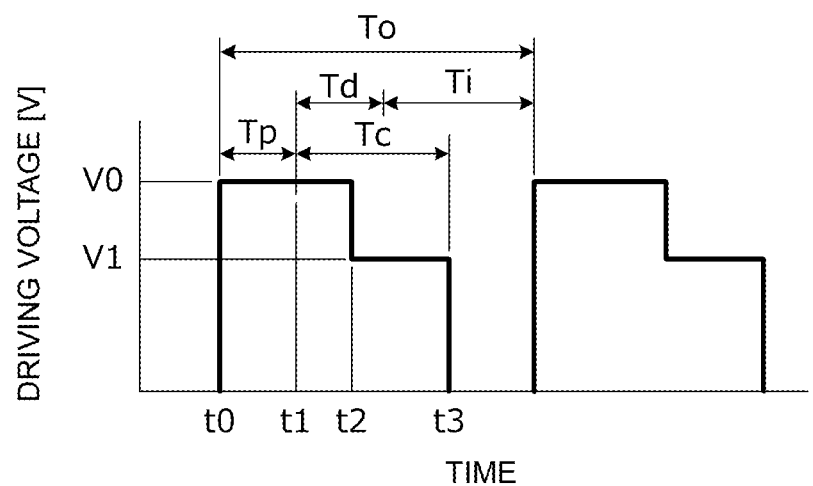
FIG. 7 is a graph illustrating an example of a change in the driving voltage of a piezoelectric pump in a second embodiment.

FIG. 7 is a graph illustrating an example in which the driving voltage is changed during the cooling period. The vertical axis represents the driving voltage of the piezoelectric pump 20, and the horizontal axis represents time. In FIG. 7, a pressurization period is denoted by Tp, a cooling period is denoted by Tc, and an operating period is denoted by To. Furthermore, an exhaust period is denoted by Td, and an interval period is denoted by Ti.

In the example of FIG. 7, at time t0, the valve 60 is closed, the piezoelectric pump 20 starts to be driven, and the cuff 70 is pressurized over the pressurization period Tp. After that, the valve is opened at time t1, and air in the cuff 70 is thus gradually exhausted over the exhaust period Td. Furthermore, even after the valve is opened at the time t1, the driving voltage of V0 is maintained until time t2. The driving voltage is changed to V1 at the time t2, and the driving voltage of V1 is maintained until time t3. The operating period To is equal to the sum of (pressurization period Tp), (exhaust period Td), and (interval period Ti).

As described in this example, the driving voltage may be changed during the cooling period Tc. The times t1 and t2 illustrated in FIG. 7 may be set in a fixed manner in advance. However, the driving voltage may be changed under the condition that the temperature of the piezoelectric pump is decreased to a predetermined value.

In FIG. 7, the driving of the piezoelectric pump is stopped at the time t2. After that, the piezoelectric pump, the flow passage, and air in the flow passage are naturally dissipated.

Figure 8:
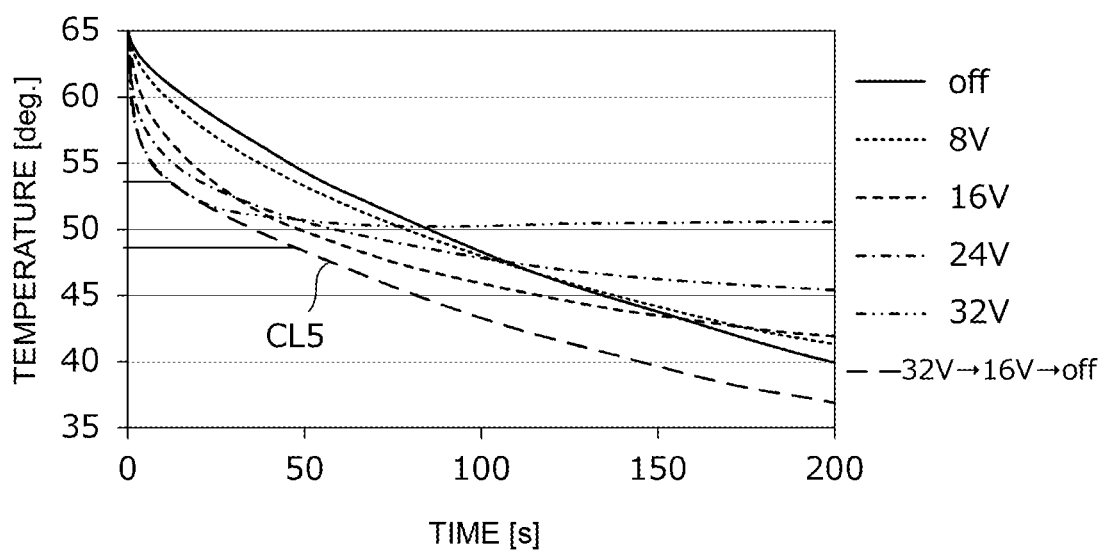
FIG. 8 is a graph illustrating an improvement in cooling effects of the piezoelectric pump 20 in a case where the driving voltage is changed during a cooling period.

FIG. 8 is a graph illustrating an improvement in the cooling effects of the piezoelectric pump 20 in a case where the driving voltage is changed during the cooling period. In FIG. 8, the vertical axis represents the temperature of the piezoelectric pump 20, and the horizontal axis represents time (elapsed time). A characteristics line CL5 represents an example in which the piezoelectric pump is driven at 32 V within a range from 64 degrees C. to 53 degrees C. and then driven at 16 V within a range up to 48 degrees C., and the driving of the piezoelectric pump is then stopped. As is clear from a comparison with another example in which the driving voltage is not changed during the cooling period, reducing the driving voltage in accordance with a decrease in the temperature increases the cooling effects.

Figure 9:
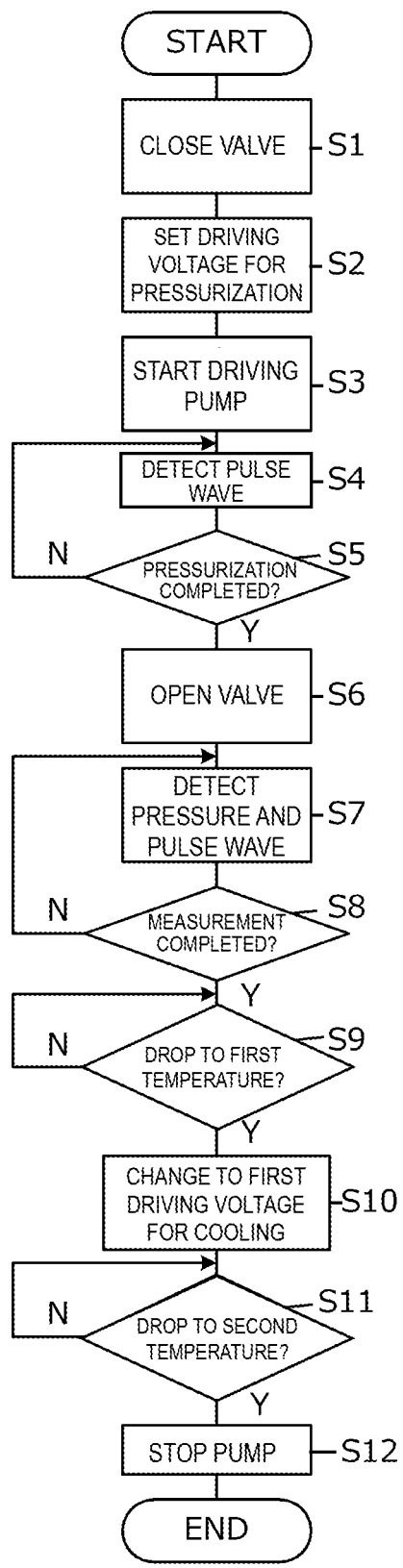
FIG. 9 is a flowchart illustrating a procedure of a process of a controller 90 for changing the driving voltage according to the temperature during the cooling period.

FIG. 9 is a flowchart illustrating a procedure of a process of the controller 90 for changing the driving voltage according to the temperature during the above-mentioned cooling period. Operations of the fluid control device 101 and the sphygmomanometer 201 will be explained below with reference to FIG. 9.

The processing details from steps S1 to S8 are the same as those in the first embodiment illustrated in FIG. 4. First, the valve 60 is closed, a driving voltage for pressurization (in the example described above, 32 V) is set, and the piezoelectric pump 20 is driven at the set voltage (S1→S2→S3). Accordingly, air is sent to the cuff 70, and the pressurization starts.

After that, when the cuff 70 reaches a predetermined pressure, the valve 60 is opened (S4→S5→S6). Accordingly, the air in the cuff 70 is gradually exhausted and decompressed. During the decompression, the maximum blood pressure and the minimum blood pressure are measured (S7→S8).

After that, a detection value of the temperature sensor 81 is read, and the process waits until the temperature of the piezoelectric pump 20 reaches a first temperature (in the example described above, 53 degrees C.) (S9). When the temperature of the piezoelectric pump 20 decreases to the first temperature, the driving voltage is changed to a first driving voltage for cooling (in the example described above, 16 V), and the process waits until the temperature of the piezoelectric pump 20 reaches a second temperature (in the example described above, 48 degrees C.) (S10→S11). When the temperature of the piezoelectric pump 20 decreases to the second temperature, the driving voltage is set to 0 V. That is, the driving of the piezoelectric pump is stopped.

In the example illustrated in FIG. 9, the driving voltage for the cooling period is set in accordance with the comparison among the temperature of the piezoelectric pump, the first temperature, and the second temperature. However, the driving voltage for the cooling period may be set by obtaining a difference between the temperature of the piezoelectric pump and the ambient temperature and comparing the temperature difference with a predetermined value. For example, in the case where the temperature difference mentioned above decreases to a first temperature difference in step S9 in FIG. 9, the driving voltage may be changed to the first driving voltage for cooling, and in the case where the temperature difference decreases to a second temperature difference in step S11, the driving of the piezoelectric pump may be stopped.

Furthermore, after the pressurization period ends, a difference between the temperature of the piezoelectric pump and the ambient temperature may be obtained. In the case where the temperature difference does not reach a predetermined value, that is, in the case where the temperature is not high enough to require cooling, the piezoelectric pump may be stopped immediately.

The driving voltage may be changed in multiple stages during the cooling period.

According to the second embodiment, as the temperature decreases, lower power is supplied to the pump, and a smaller amount of heat is generated by the driving of the pump. Thus, a high cooling effect of the pump can be achieved. Therefore, the interval period Ti illustrated in FIG. 7 may be short, and the operating period To for repetitive operation can be shortened.

Third Embodiment

In a third embodiment, an example in which driving voltage is gradually changed during a cooling period is described. The basic configuration of a fluid control device and a sphygmomanometer according to the third embodiment is the same as that described in the first embodiment.

Figure 10:
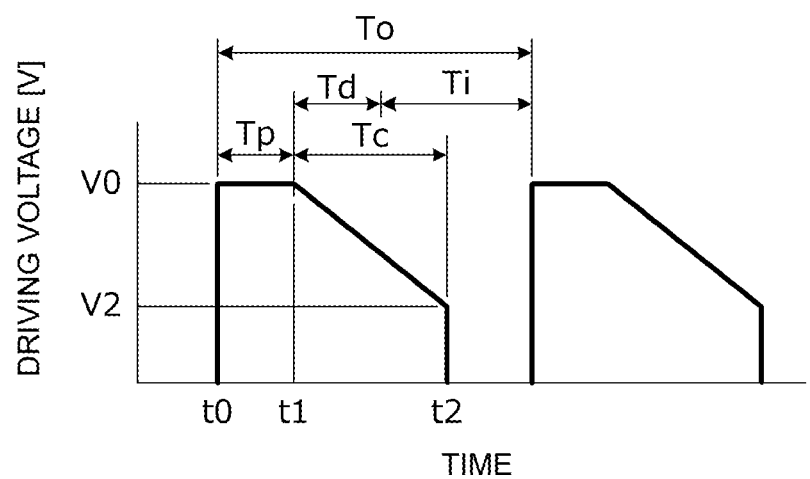
FIG. 10 is a graph illustrating an example of a change of a driving voltage of a piezoelectric pump in a third embodiment.

FIG. 10 illustrates an example in which the driving for the pressurization starts at a driving voltage of V0 at time t0, pressurization ends at time t1, and then, the driving voltage is gradually reduced from V0 to V2 until time t2. The vertical axis represents the driving voltage of the piezoelectric pump 20, and the horizontal axis represents time. In FIG. 10, a pressurization period is denoted by Tp, a cooling period is denoted by Tc, and an operating period is denoted by To. Furthermore, an exhaust period is denoted by Td, and an interval period is denoted by Ti.

Figure 11:
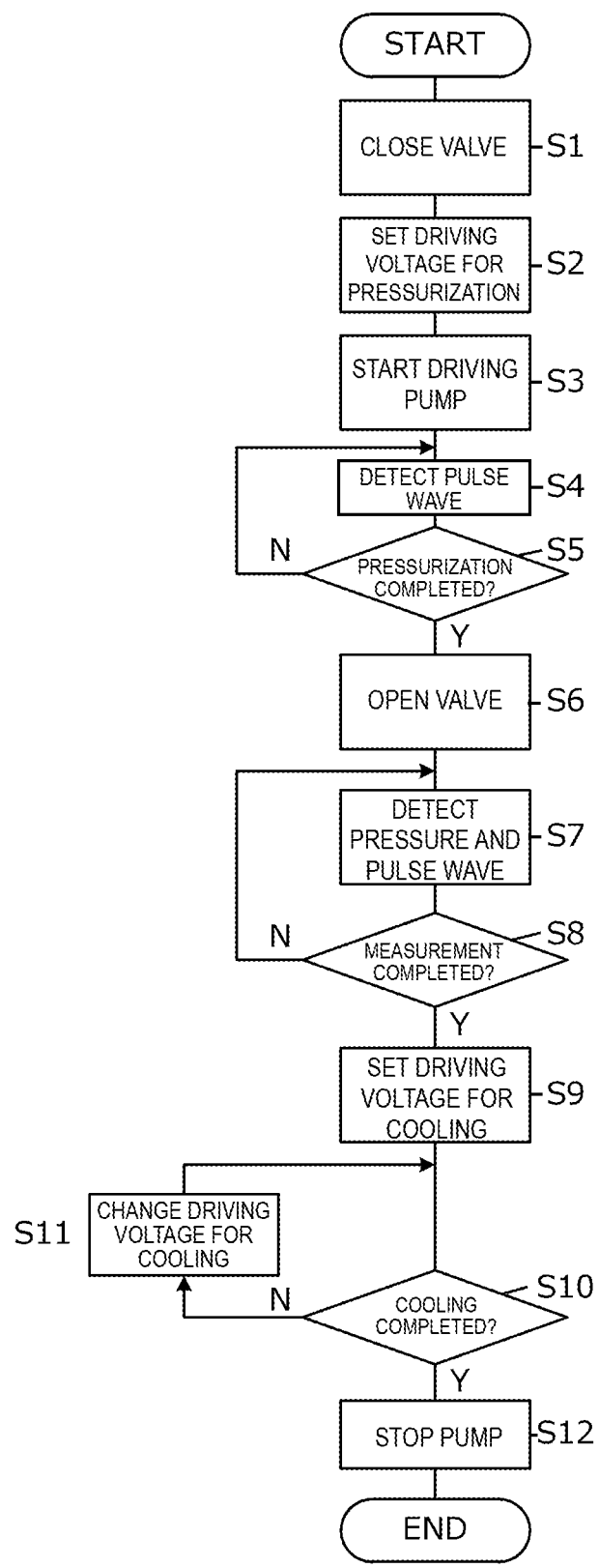
FIG. 11 is a flowchart illustrating a procedure of a process of a controller 90 in the third embodiment.

FIG. 11 is a flowchart illustrating a procedure of a process of the controller 90 according to the third embodiment. Operations of the fluid control device 101 and the sphygmomanometer 201 will be explained below with reference to FIG. 11.

The processing details from steps S1 to S8 are the same as those in the first embodiment illustrated in FIG. 4. First, the valve 60 is closed, a driving voltage for pressurization (in the example described above, 32 V) is set, and the piezoelectric pump 20 is driven at the set voltage (S1→S2→S3). Accordingly, air is sent to the cuff 70, and the pressurization starts.

After that, when the cuff 70 reaches a predetermined pressure, the valve 60 is opened (S4→S5→S6). Accordingly, the air inside the cuff 70 is gradually exhausted and decompressed. During the decompression, the maximum blood pressure and the minimum blood pressure are measured (S7→S8).

After that, the driving voltage is changed to a driving voltage for cooling (S9). However, in the example illustrated in FIG. 10, the driving voltage for cooling is equal to the driving voltage for pressurization (32 V).

After that, a detection value of the temperature sensor 81 is read, and the driving voltage is gradually decreased until the temperature of the piezoelectric pump 20 decreases to a predetermined value (S10→S11→S10). When the temperature of the piezoelectric pump 20 decreases to the predetermined value, the driving voltage is set to 0 V. That is, the driving of the piezoelectric pump is stopped.

Fourth Embodiment

In a fourth embodiment, an example in which power to be supplied to a piezoelectric pump is not changed by driving voltage but is changed by the duty ratio of the driving of the piezoelectric pump or by driving the piezoelectric pump intermittently, is described.

Figure 12A:
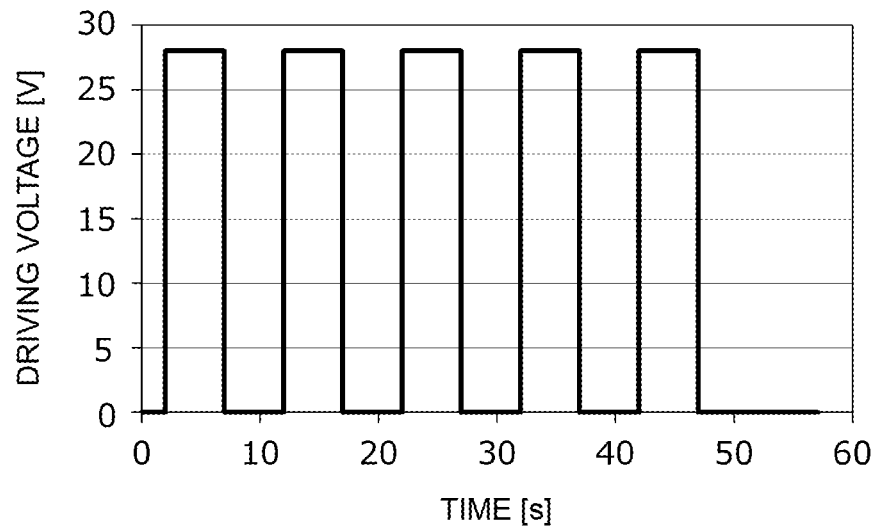
FIGS. 12A and 12B are graphs illustrating a change of a driving voltage of a piezoelectric pump in a fourth embodiment.
Figure 12B:
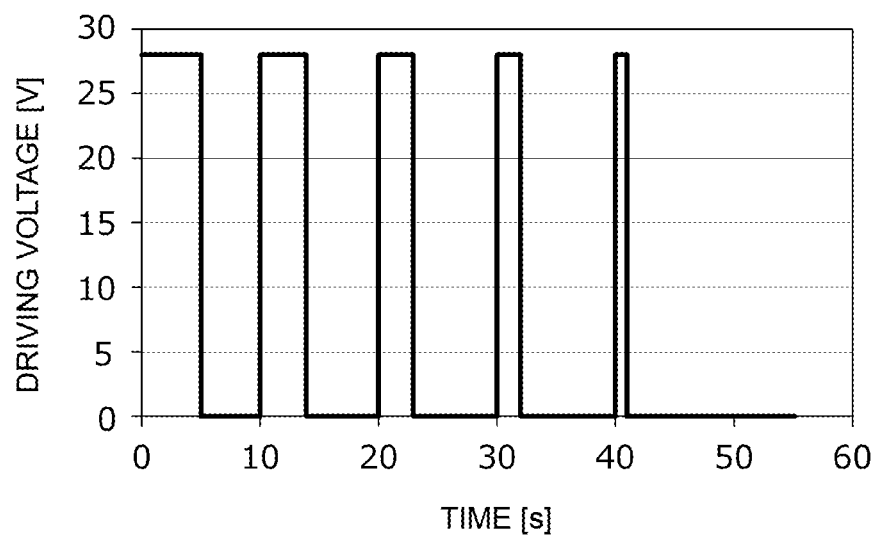

FIGS. 12A and 12B are graphs illustrating a change of the driving voltage of the piezoelectric pump. FIG. 12A illustrates an example of the intermittent driving in which the driving voltage is set to 28 V and the driving/stopping is repeated every 50 seconds. This is also an example of the driving with an ON duty ratio of 50%. FIG. 12B illustrates an example in which the driving voltage is set to 28 V and the ON duty ratio gradually decreases in periods of 10 seconds.

In the example of FIG. 12A, the piezoelectric pump is driven with the average driving power which is half of that of the case where the piezoelectric pump is continuously driven at 28 V. In the example of FIG. 12B, the piezoelectric pump is driven with the power gradually decreasing from the average driving power which is half of that of the case where the piezoelectric pump is continuously driven at 28 V.

In the examples of FIGS. 12A and 12B, a period is set to ten seconds. However, for example, the duty ratio may be controlled in short periods of about one-tenth seconds.

The fluid control device and the sphygmomanometer according to the fourth embodiment that are intermittently driven or for which the duty ratio is controlled are configured in a similar manner by replacing the control of the driving voltage described above in each of the foregoing embodiments with the control of the duty ratio.

In the example illustrated in FIG. 12A, the piezoelectric pump is not driven immediately after the cooling period starts. As described above, when the pressurization period ends and the cooling period starts, the piezoelectric pump may be temporarily stopped.

Fifth Embodiment

In a fifth embodiment, some examples of the connection relationship of a pump, a valve, and a container are explained.

Figure 13A:
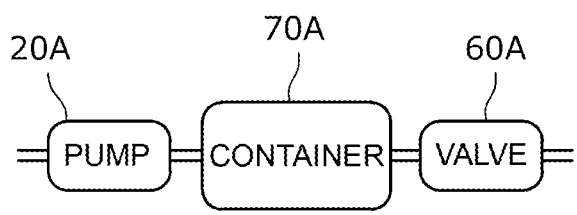
FIGS. 13A and 13B are diagrams illustrating the connection relationship of a pump, a container, and a valve in a fluid control device according to a fifth embodiment.
Figure 13B:
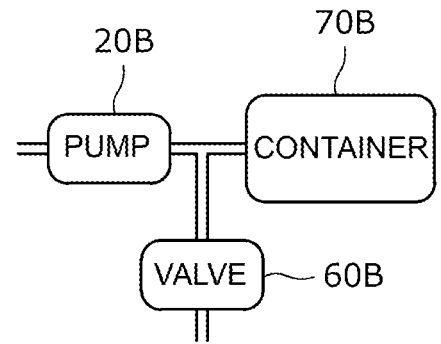

FIG. 13A illustrates an example in which a pump 20A, a container 70A, and a valve 60A are connected in series in this order. FIG. 13B illustrates an example in which a pump 20B, a container 70B, and a valve 60B are connected to a common flow passage. The valves 60A and 60B are two-port valves.

With either the structure of FIG. 13A or FIG. 13B, the valve 60A is closed and the pump 20A is driven during the pressurization period. During the cooling period, the valve 60A is opened while the driving of the pump 20A is maintained. An operation of cooling is similar to those in the foregoing embodiments.

In the case where multiple piezoelectric pumps are connected in series, the foregoing embodiments may be applied to only a part of the piezoelectric pumps. The piezoelectric pump in the first embodiment requires a power consumption of 0.46 W to obtain a flow rate of 0.77 L/min. Therefore, in the case where two piezoelectric pumps are connected in series and both the piezoelectric pumps are driven during the exhaust, a total power consumption of 0.92 W is required to obtain a flow rate of 0.77 L/min. In contrast, in the case where only one of the piezoelectric pumps is driven, the total power consumption is 0.46 W. In the case where the flow passage resistance of the other one of the piezoelectric pumps that is stopped is large, the driving voltage needs to be increased to obtain an equivalent flow rate. However, even in such a case, a power consumption of only 0.55 W is required. As described above, by driving one of the piezoelectric pumps and stopping the other one of the piezoelectric pumps during the exhaust, a power consumption required for cooling can be decreased. In addition, the amount of the heat generated by driving decreases, and cooling effects can thus be increased.

Other Embodiments

In the foregoing embodiments, in FIGS. 4, 9, and 11, examples in which blood pressure is measured in the process of decompression of a cuff are described. However, blood pressure may be measured in the process of pressurization, and after that, a valve may be opened.

In each of the foregoing embodiments, an example in which a piezoelectric pump pressurizes a cuff is described. However, this configuration may be applied in a similar manner to an air mattress or the like as well as a cuff.

Furthermore, in each of the foregoing embodiments, an example in which a piezoelectric pump is a pressurization pump that discharges air and supplies the air to a container (cuff) and the container is thus pressurized is described. However, the present disclosure is also applicable in a similar manner to a fluid control device in which a piezoelectric pump is a decompression pump that sucks air and causes air inside a container to be exhausted and the container is thus decompressed. For example, the present disclosure may also be applied to a milking device, a nasal aspirator, and the like.

Furthermore, a "pump" according to the present disclosure is not limited to a piezoelectric pump. The present disclosure is also applicable in a similar manner to any pump that generates heat when it is driven.

Furthermore, a "pump" according to the present disclosure is not limited to a pump (blower) that transports air. The present disclosure is also applicable in a similar manner to a pump that transports liquid.

Means for detecting the temperature of a piezoelectric pump is not limited to a configuration in which the temperature sensor 81 is added to the piezoelectric pump. A temperature sensor may be arranged at a predetermined position in the casing of a fluid control device so that the temperature of the piezoelectric pump can be detected indirectly based on a detection value of the temperature sensor. For example, a temperature sensor may be provided to detect the temperature of fluid.

Finally, the forgoing embodiments are mere exemplifications in all aspects, and the present disclosure is not limited to these exemplifications. Modifications and changes may be made in an appropriate manner by those skilled in the art. The scope of the present disclosure is not defined by the foregoing embodiments but is defined by the scope of the Claims. Furthermore, the scope of the present disclosure covers changes from embodiments within the scope of the Claims and the scope of equivalents.

BAT . . . power
P0, P1, and P2 . . . port
Tc . . . cooling period
Td . . . exhaust period
Ti . . . interval period
To . . . operating period
Tp . . . pressurization period
10 . . . driving circuit
11 . . . DC/DC converter
12 . . . switch
13 . . . self-vibrating circuit
20 . . . piezoelectric pump (pump)
20A and 20B . . . pump
21 . . . piezoelectric pump
22 . . . cover plate
23 . . . flow passage plate
24 . . . opposing plate
25 . . . adhesive layer
26 . . . vibration plate
27 . . . piezoelectric element
28 . . . insulation plate
29 . . . power supply plate
30 . . . spacer plate 31 . . . roof plate
33 . . . suction port
34 . . . discharge port
35 and 36 . . . external connection terminal
37 . . . flow passage hole
38 . . . cavity
39 . . . movable part
40 and 46 . . . pump room
41 . . . central part
42 . . . hitting part
43 . . . connecting part
44 . . . frame part
45 . . . internal connection terminal
50 . . . driving control circuit
51 . . . driving voltage control unit
52 . . . duty ratio control unit
60, 60A, and 60B . . . valve
70 . . . cuff (container)
70A . . . container
81 . . . temperature sensor
82 . . . pressure sensor
83 . . . pulse wave sensor
90 . . . controller
101 . . . fluid control device
201 . . . sphygmomanometer

The invention claimed is:

1. A fluid control device comprising:
a pump;
a container that is pressurized or decompressed by the pump;
a valve that is configured to control fluid communication between the container and an outside of the container; and
a controller configured to control operation of the pump and the valve,
wherein in a first control mode, the controller is configured to cause the valve to enter a closed state and drive the pump, thereby pressurizing or decompressing the container, and
wherein in a second control mode, the controller is configured to cause the valve to enter an opened state in which the pump and the container concurrently communicate with the outside of the container and drive the pump, thereby causing the pump to cool down, and
wherein the controller is configured to first operate in the first control mode and then to operate in the second control mode.

2. The fluid control device according to claim 1, wherein:
the controller is further configured to change a driving power of the pump between operation in the first control mode and operation in the second control mode, and
the driving power of the pump is a power when the pump is continuously driven or is an average power when the pump is periodically driven.

3. The fluid control device according to claim 2, wherein during operation in the second control mode, the controller is configured to set the driving power for the pump to be greater than during operation in the first control mode.

4. The fluid control device according to claim 2, wherein during operation in the second control mode, the controller is configured to set the driving power for the pump to be less than during operation in the first control mode.

5. The fluid control device according to claim 4, wherein after switching from the first control mode to the second control mode, the controller is configured to reduce the driving power for the pump in a step-wise manner.

6. The fluid control device according to claim 2, wherein the controller is configured to change the driving power for the pump by changing a driving voltage of the pump.

7. The fluid control device according to claim 2, wherein the controller is configured to change the driving power for the pump by changing a duty ratio of driving of the pump.

8. The fluid control device according to claim 2, wherein the controller is configured to change the driving power for the pump by intermittently driving the pump.

9. The fluid control device according to claim 2, wherein:
the controller is configured to change the driving power for the pump after causing the valve to change from the closed state to the opened state, and
the driving power is changed in accordance with a temperature of the pump or in accordance with a difference between the temperature of the pump and an ambient temperature.

10. The fluid control device according to claim 1, wherein the controller is configured to stop the pump after a predetermined period of time since causing the valve to change from the closed state to the opened state.

11. The fluid control device according to claim 1, wherein after causing the valve to change from the closed state to the opened state, the controller is configured to stop the pump in accordance with a temperature of the pump or in accordance with a difference between the temperature of the pump and an ambient temperature.

12. The fluid control device according to claim 1, wherein the controller is configured to drive the pump after the controller causes the valve to change from the closed state to the opened state, and when a temperature of the pump is greater than a predetermined value or when the temperature of the pump is greater than an ambient temperature by at least a predetermined amount.

13. The fluid control device according to claim 1, wherein the pump is a piezoelectric pump that causes fluid transport by vibrations of a piezoelectric element.

14. The fluid control device according to claim 1, further comprising:
a second pump that is connected in series with the pump,
wherein the controller is configured to operate in the second control mode during a time in which the second pump is stopped.

15. A sphygmomanometer comprising:
the fluid control device of claim 1;
a pressure sensor configured to detect a pressure of the container;
and a blood flow sensor configured to detect a state of a blood flow,
wherein the container is a cuff, and
wherein the controller is configured to measure blood pressure based on the pressure of the container detected by the pressure sensor and the blood flow state detected by the blood flow sensor, while pressurizing the cuff by causing the valve to clause and driving the pump, and while decompressing the cuff by causing the valve to open.

16. The fluid control device according to claim 1, wherein during operation in the first control mode, the valve does not cause communication between the container and the outside of the container, and
wherein during operation in the second control mode, the valve causes communication between the container and the outside of the container.

* * * * *